US011439720B2

(12) United States Patent
Robinson

(10) Patent No.: US 11,439,720 B2
(45) Date of Patent: Sep. 13, 2022

(54) METHOD AND APPARATUS TO EVALUATE INTERNAL FLEXIBLE ENDOSCOPE CHANNELS IN THE CONTEXT OF ENDOSCOPE PORTS AND CHANNEL COMPLEXITIES

(71) Applicant: American Sterilizer Company, Mentor, OH (US)

(72) Inventor: Nancy A. Robinson, Mentor, OH (US)

(73) Assignee: American Sterilizer Company, Mentor, OH (US)

( * ) Notice: Subject to any disclaimer, the term of this patent is extended or adjusted under 35 U.S.C. 154(b) by 437 days.

(21) Appl. No.: 16/542,734

(22) Filed: Aug. 16, 2019

(65) Prior Publication Data
US 2021/0046206 A1   Feb. 18, 2021

(51) Int. Cl.
| A61L 2/00 | (2006.01) |
| B08B 9/04 | (2006.01) |
| C12Q 1/02 | (2006.01) |
| A61L 2/28 | (2006.01) |
| A61B 90/70 | (2016.01) |
| A61B 1/12 | (2006.01) |

(52) U.S. Cl.
CPC ............... *A61L 2/28* (2013.01); *A61B 1/121* (2013.01); *A61B 90/70* (2016.02); *A61B 2090/701* (2016.02); *A61B 2090/702* (2016.02); *A61L 2202/24* (2013.01)

(58) Field of Classification Search
CPC ....... A61B 1/123; B08B 9/032; A61L 2/0088; A61L 2/16; A61L 2/18; A61L 2/24; A61L 2202/24

USPC ........ 435/29; 422/28, 68.1, 82.05, 119, 292, 422/300; 134/8, 56 R
See application file for complete search history.

(56) References Cited

U.S. PATENT DOCUMENTS

| 6,734,958 B1 | 5/2004 | MacKinnon et al. |
| 8,083,861 B2 | 12/2011 | Labib |
| 10,201,269 B2 | 2/2019 | Yang et al. |
| 2003/0012688 A1* | 1/2003 | Kippenhan, Jr. ......... A61L 2/18 422/28 |
| 2007/0286764 A1 | 12/2007 | Noguchi et al. |

(Continued)

FOREIGN PATENT DOCUMENTS

| GB | 2568304 A | 5/2019 |
| WO | WO 03/028772 A1 | 4/2003 |
| WO | WO 2018/013204 A1 | 1/2018 |

OTHER PUBLICATIONS

International Search Report and Written Opinion dated Nov. 26, 2020 from related/corresponding PCT Patent Appl. No. PCT/US20/45860, filed Aug. 12, 2020.

(Continued)

*Primary Examiner* — Monzer R Chorbaji
(74) *Attorney, Agent, or Firm* — Kusner & Jaffe

(57) ABSTRACT

A test instrument and a method for producing a test instrument used to evaluate a cleaning, disinfection and/or drying processes of internal flexible channels includes obtaining a medical instrument having a flexible probe section configured for insertion into a body, the flexible probe section including at least one internal flexible channel and at least one external device port, and attaching an access device between the at least one external device port and the at least one internal flexible channel to enable selective access into the internal flexible channel.

27 Claims, 6 Drawing Sheets

(56) References Cited

U.S. PATENT DOCUMENTS

| | | |
|---|---|---|
| 2012/0073614 A1 | 3/2012 | Otani et al. |
| 2013/0233236 A1* | 9/2013 | Walta .................. A61B 90/70 |
| | | 116/201 |
| 2017/0332891 A1 | 11/2017 | Yang et al. |
| 2018/0071418 A1 | 3/2018 | Bommarito |

OTHER PUBLICATIONS

Marek et al., "Endoscopy supply water and final rinse testing: five years of experience," Journal of Hospital Infection, 88(4), 2014, pp. 207-212.

Beilenhoff et al., "ESGE-ESGENA guideline: cleaning and disinfection in gastrointestinal endoscopy," Endoscopy, 2018, 40(11), pp. 939-957.

Jolly et al., "Better instructions for use to improve reusable medical equipment (RME) sterility," Human factors, 55(2), 2013, pp. 397-410.

* cited by examiner

| Process Type | Methods to Introduce "Contamination" | Test to Determine Efficacy of Process |
|---|---|---|
| Drying of Flexible Endoscope | • Perform a cleaning evaluation as instructed by the device manufacturer to introduce fluids into the channels<br>• Use syringes to flush colored water or alcohol through the endoscope channels<br>• Place test article into an endoscope processor and perform a cycle (may or may not have a drying phase as part of the cycle) or place test article into a drying cabinet and perform a drying cycle. | • Visual assessment of channels for residual water<br>• Weight before and after subjecting to process<br>• Flush through channels with dry compressed air and aim the discharge at:<br>   ○ a mirror. Misting of mirror or discharge of visible drops indicates the channel is not dry.<br>   ○ a horizontal piece of anhydrous copper [II] sulfate paper. Color change indicates presence of moisture.<br>   ○ A horizontal piece of white absorptive paper. Paper will show color of the colored water/alcohol. |
| Disinfection of Flexible Endoscope | • Place biological indicators or liquid inoculum containing at least $10^6$ colony forming units of the challenge organism into each of the channel systems using a normal opening or by opening the channel (loosen screws already part of the design of the test article or open a "quick connect" that was introduced into the test article.<br>   ○ Push the BI to the challenge location using a flexible tube or an endoscope cleaning brush.<br>   ○ Introduce liquid inoculum using a tube to direct the liquid to the challenge site | • Microbiological culturing of the BI removed from the channel. The channel is cut near the BI and the BI removed using sterile forceps and placed into culture media or it is tipped into a tube of culture media. Determine if growth of the organism occurs.<br>• Excise the section of the channel directly challenged with the liquid inoculum and place in culture media. Determine if growth of the organism occurs. |
| Biofilm Removal | • Place a section of tubing, which has been cultured to grow a biofilm within the tubing, into the test article. The biofilm-containing tube may be attached using a screw fitting which is part of the endoscope design or a "quick connect" that is introduced into the design | • Remove introduced section from the test article and cut into pieces.<br>   ○ Evaluated via scanning electron microscopy (SEM) for remaining biofilm<br>   ○ Flush tube sections with harvest media (for example water) and evaluate flush for some or all of the following:<br>      ■ Total Organic Carbon (TOC)<br>      ■ Protein<br>      ■ Hemoglobin<br>      ■ Carbohydrate<br>   ○ Place section in growth media and evaluate for growth<br>   ○ Visualize with biofilm stain (various dyes can be used including crystal violet and methyl blue) |

FIG. 7

METHOD AND APPARATUS TO EVALUATE INTERNAL FLEXIBLE ENDOSCOPE CHANNELS IN THE CONTEXT OF ENDOSCOPE PORTS AND CHANNEL COMPLEXITIES

FIELD OF THE INVENTION

The present invention relates generally to decontamination evaluations of medical instruments and, more particularly, to a test instrument for evaluating the effectiveness of cleaning, disinfection/sterilization and drying processes in a medical context and a method for making such test instrument.

BACKGROUND OF THE INVENTION

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

Since in the medical field endoscopes are inserted into a body cavity for examinations and treatments, the endoscope requires cleaning, disinfection (high level disinfection or sterilization) and drying after each use (collectively referred to as decontamination processes). As such, various methods of endoscope decontamination have been and are being developed. In confirming the effectiveness of such decontamination methods, the endoscope is subjected to the process, and then an evaluation is performed to determine if the decontamination process meets predetermined criteria for cleanliness.

Currently, cleaning of soils and biofilm, disinfection, and drying evaluations for flexible endoscope channels are performed using various devices, including Teflon® tubing, endoscope surrogate devices, and intact flexible endoscopes. When using Teflon® tubing to model an endoscope, an internal diameter and length of the tubing is selected to match an internal diameter and length of that used in an actual endoscope. A problem with such simple tubing model is that it does not allow evaluation of the complexities present in real device channels. Specifically, such tubing does not have i) ports that connect internal channels with the exterior of the device or ii) internal connections along a length of a channel (e.g., connections that join air and water channels in an insertion tube section of the endoscope, the joined channel then connecting to a nozzle). As a result of these deficiencies, evaluations performed with the simple tubing model may not provide accurate or compelling performance data.

Regarding endoscope surrogate devices, these devices are test articles designed to represent construction elements of endoscope-specific characteristics affecting the flow conditions in endoscope channels (as defined in ISO 15883-4). As discussed in ISO 15883-4 Annex C, the surrogate devices are similar to actual endoscopes but some aspects remain different (e.g., trumpet valves, connectors). Further, all interior design aspects of actual endoscopes are not included in the endoscope surrogate. For example, the described surrogates do not include distal tip connections, junctions present in insertion tube sections of the air and water channels (that allow easy replacement of the channels during service) and the junctions/connections within the light guide connector. Therefore, the surrogates do not represent the full complexity of a real endoscope.

Regarding a flexible endoscope, conventional endoscopes do not permit access to the internal channels, which is needed for one or more of i) preparing the test, growing a biofilm in the channels, placing a biological indicator (BI), for example a wire inoculated with organism, within all channel systems, ii) visualization of the process/results, for example visually determining if channels are clean and/or dry, and iii) destructive preparation of samples of channels, for example for electron microscopy.

Accordingly, there is a need in the art for a test instrument that closely mimics characteristics of an actual endoscope and also provides access to internal channels for performing decontamination evaluations.

SUMMARY OF THE INVENTION

In accordance with embodiments of the present invention, there is provided a test instrument and method of making such test instrument that enables both physical and visual access to ports and internal channels of the test instrument for decontamination evaluations, where the device mimics ports and channels of an actual medical instrument, such as a flexible endoscope. The test instrument and method of making the test instrument in accordance with the invention provide a realistic test article that incorporates the complexities of a real flexible endoscope, thereby enabling the type of evaluations performed using simple tubing models and surrogates.

According to one aspect of the invention, a method for producing a test instrument used to evaluate at least one of a cleaning, disinfection or drying process of internal flexible channels includes: obtaining a medical instrument having a flexible probe section configured for insertion into a body, the flexible probe section including at least one internal flexible channel and at least one external device port; and attaching an access device between the at least one external device port and the at least one internal flexible channel to enable selective access into the internal flexible channel.

In one embodiment, attaching the access device comprises removing an exterior sheath from the flexible probe section to expose the at least one external device port and the at least one internal flexible channel of the medical instrument.

In one embodiment, attaching the access device comprises replacing the flexible probe section with transparent tubing, the transparent tubing defining the at least one flexible internal channel.

In one embodiment, attaching the access device comprises using at least one of a tubing connector or a threaded connector as the access device.

In one embodiment, obtaining the medical instrument comprises obtaining a medical instrument that has at least one of exceeded a predetermined service life or become inoperable.

In one embodiment, the medical instrument comprises a handle section for operating the medical instrument, the handle section connected to the flexible probe section, wherein attaching the access device comprises placing the access device within the handle section.

In one embodiment, attaching the access device comprises attaching a valve cylinder in the handle section to provide selective access to the at least one channel.

In one embodiment, obtaining the medical instrument comprises obtaining a flexible endoscope having a flexible probe section with a distal end surface configured for insertion into a body, the distal end surface including one external port of the at least one external port fluidically coupled to one internal channel of the at least one internal channel.

In one embodiment, the at least one external port comprises at least one of a port for outputting a liquid, port for outputting air, or a port for evacuating the fluid or the air.

According to another aspect of the invention, a method for evaluating internal flexible endoscope channels includes: forming a test instrument according to the method described herein; introducing, via the access device, at least one contaminant to at least a portion of the test instrument; performing a decontamination step on the test instrument; and evaluating the test instrument to determine if the decontamination step produced a predetermined level of removal/destruction of the contaminant.

In one embodiment, introducing the at least one contaminant comprises introducing a fluid into the test instrument.

In one embodiment, performing the decontamination step comprises exposing the test instrument to a drying process.

In one embodiment, evaluating the test instrument comprises at least one of performing a visual inspection for residual contaminant in the at least one channel, determining the presence of the at least one contaminant in the test instrument based on a weight of the test instrument before introducing the at least one contaminant and a weight of the test instrument after performing the decontamination step, or exposing the test instrument to dry compressed air and capturing residual contaminant expelled from the test instrument.

In one embodiment, introducing the at least one contaminant comprises placing at least one of a liquid inoculum or biological indicators containing a challenge organism into the test instrument.

In one embodiment, placing the biological indicators comprises inserting the at least one of the liquid inoculum or biological indicators into the test instrument via the access device.

In one embodiment, inserting the biological indicators comprises opening the access device and inserting the at least one of the liquid inoculum or the biological indicators into the at least one channel of the test instrument via the access device.

In one embodiment, performing the decontamination step comprises disinfecting the test instrument.

In one embodiment, evaluating the test instrument comprises removing the biological indicators from the test instrument and placing the removed biological indicators into a culture media.

In one embodiment, introducing the at least one contaminant comprises growing a biofilm within a section of tubing, and inserting the tubing into the test instrument.

In one embodiment, the access device comprises at least one of a screw fitting or a quick connect of the test instrument.

In one embodiment, performing the decontamination step comprises removing the biofilm from the test instrument.

In one embodiment, evaluating the test instrument comprises at least one of evaluating the test instrument for remaining biofilm, flushing sections of the test instrument with a harvest media and evaluating the flushed harvest media for the presence of a predetermined components, placing the removed biofilm in a growth media and evaluating for further growth, or applying a biofilm stain to identify the presence of the biofilm.

According to another aspect of the invention, a test instrument for performing at least one of a cleaning, sterilization, or drying evaluation includes: a handle; a flexible probe configured for insertion into a body, the flexible probe including a proximal end connected to the handle, at least one port, and at least one flexible internal channel, the at least one port connecting the at least one flexible internal channel to an exterior of the test instrument; and an access device connected to the at least one internal channel and configured to enable selective access into the at least one flexible internal channel for insertion and/or removal of a contaminant.

In one embodiment, the test instrument includes a tip connected to a distal end of the flexible probe section, the tip including the at least one port.

In one embodiment, the access device comprises a removable junction connecting a first internal channel to both a second internal channel and a third internal channel.

In one embodiment, the removable junction comprises a Y junction.

In one embodiment, the removable junction comprises a two-port removable connector that joins at least two flexible internal channels to each other.

In one embodiment, the access devices enables visual access into the at least one flexible internal channel.

An advantage of the test instrument in accordance with present invention is the ability to visualize cleaning/drying performance in the context of a real flexible endoscope channel configuration.

Another advantage of the test instrument in accordance with the present invention is the ability to place biological indicators into the channels, and evaluate the ability of products/processes to inactivate the organisms present on the biological indicators in the context of a real flexible endoscope configuration. Further, the test instrument allows access to each channel system for direct inoculation of the channel if direct inoculation rather than a BI is used to contaminate the channel.

Yet another advantage of the test instrument in accordance with the present invention is the ability to grow a biofilm in channel sections, attach these sections to the external ports, and then evaluate the ability of products to remove and or inactivate the biofilm in the context of a real flexible endoscope configuration.

Another advantage of the test instrument in accordance with the present invention is the ability to perform destructive testing on the internal channels after evaluation in the context of a real flexible endoscope channel configuration.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 7 is a table illustrating various process steps that may be implemented to introduce a contaminant, decontaminate the instrument and evaluate whether any contaminant remains.

DETAILED DESCRIPTION OF THE INVENTION

Figure 1:
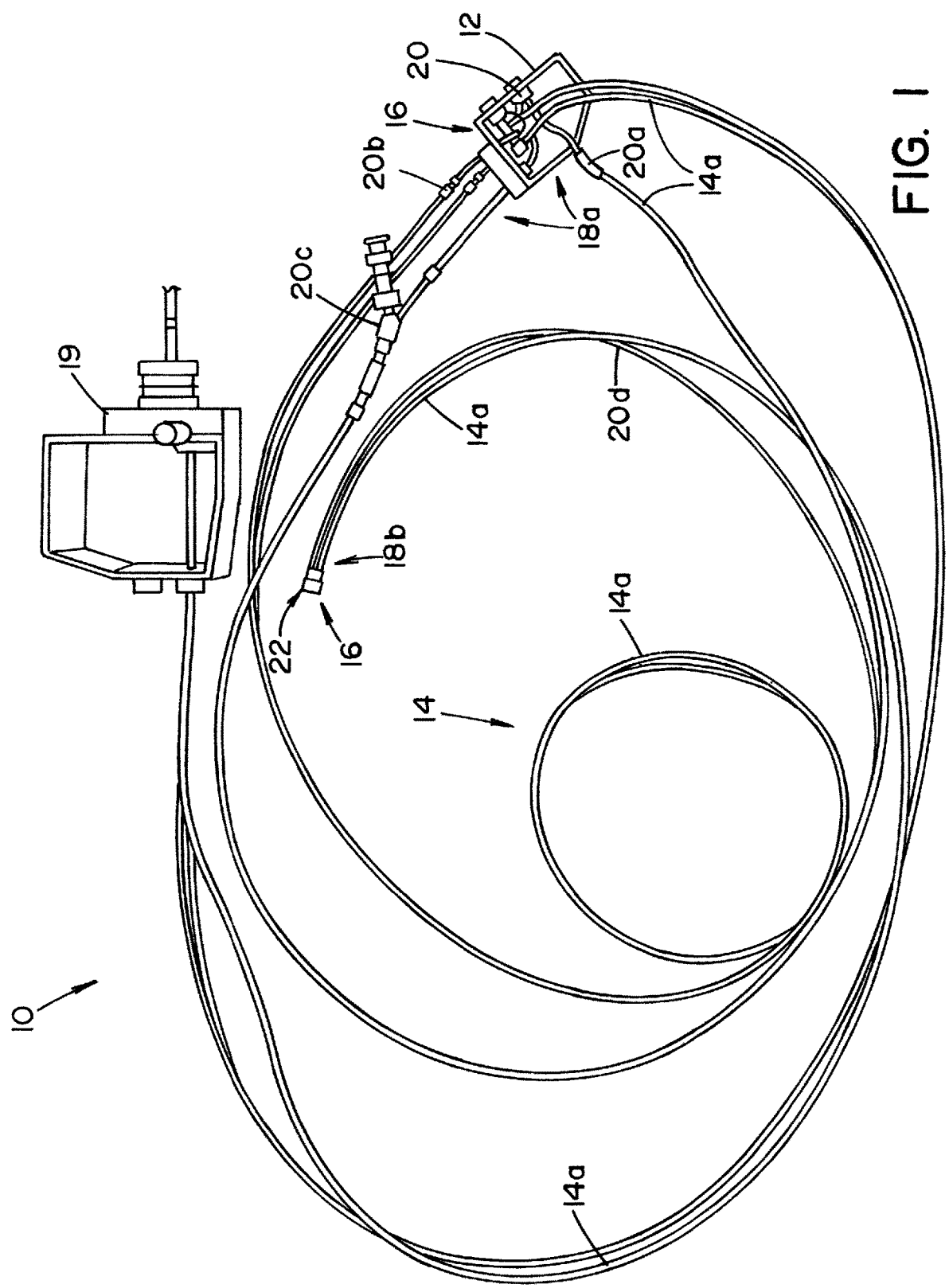
FIG. 1 illustrates an exemplary test instrument in accordance with the present invention.

Referring now to the drawings which are provided for the purposes of illustrating an embodiment of the invention only and not for the purposes of limiting same, illustrated is a test instrument for performing decontamination evaluations. As such, for ease of understanding of the invention, only the suction/instrument and air/water channels are illustrated in the figures. It should be appreciated, however, that other channel systems found in flexible endoscopes, for example auxiliary water, water jet, balloon, and elevator guide wire, are included within the scope of the invention.

Referring initially to FIG. 1, illustrated is an exemplary test instrument 10 in accordance with the present invention. The test instrument 10 may be formed, for example, from an endoscope or other like instrument. To minimize costs, it may be preferable to utilize an endoscope that has reached a predetermined end of service life and/or is no longer fully operational. The exemplary test instrument 10 includes a handle 12 and a flexible probe section 14, at least a portion of the flexible probe section 14 configured for insertion into a body. The handle 12 may include control devices such as switches, buttons and the like, for controlling suction, transferring fluids, capturing images, etc. The flexible probe section 14 includes a proximal end 18a connected to the handle 12, and one or more ports 16 that couple to an external region outside the test instrument 10 (e.g., suction ports, air/water ports). Valves may be inserted into the ports 16 and controlled using a removable valve disposed in the respective port 16 (which, for example, control the application of suction at the distal end). Valves also may be utilized in other ports 16 in the handle 12 for controlling air and water injection. Flexible internal channels 14a couple one or more ports 16 to the control devices in the handle 12. A connector 19 joins to a processor which generates light which is used when the flexible probe section 14 is inserted into a body to facilitate image capture. The image is likewise transmitted through the connector to the processor so that the image can be displayed. The connector also provides the interface for supplying air, water and suction through the instrument 10.

In accordance with one embodiment of the invention, a sheathing (not shown) of the endoscope's flexible probe section 14 is removed to expose the flexible internal channels 14a, the flexible internal channels 14a defining a path along which a fluid may flow. Access devices 20, which are defined as any device that enables selective access into a flexible channel 14a, are described in more detail below. The access devices may be spliced into the existing flexible internal channels 14a to enable configuration/reconfiguration of the channels 14a and/or to enable access into the channels 14a. In another embodiment, at least part of the flexible probe section 14 of the endoscope is removed and replaced with flexible tubing (e.g., Teflon tubing), which is connected between one or more of the ports 16 and one or more of the control devices on the handle 12.

Regardless of the embodiment, access devices 20 are inserted at predetermined locations in the flexible tubing to define a network of accessible flexible internal channels 14a connected to ports 16 and/or control devices of the test instrument 10. As noted above, the access devices 20 enable custom configuration/reconfiguration of the flexible channels 14a, including changing the diameter and/or length of the channels. To enable direct viewing of the contents within the channels 14a, a transparent material may be used to form the flexible internal channels 14a.

Thus, the instrument in accordance with the invention forms a "skeleton" of a medical instrument, such as an endoscope. Moreover, the skeleton instrument mimics features of an actual endoscope but also includes additional features that enable easy reconfiguration of the instrument, which is advantageous in that it can be readily reconfigured to mimic multiple types of endoscopes. Additionally, the skeleton instrument includes features that enable easy access into channels of the instrument, which is advantageous for inserting contaminants at various locations in the instrument and evaluating the effectiveness of cleaning/sterilization processes to remove those contaminants.

Figure 2:
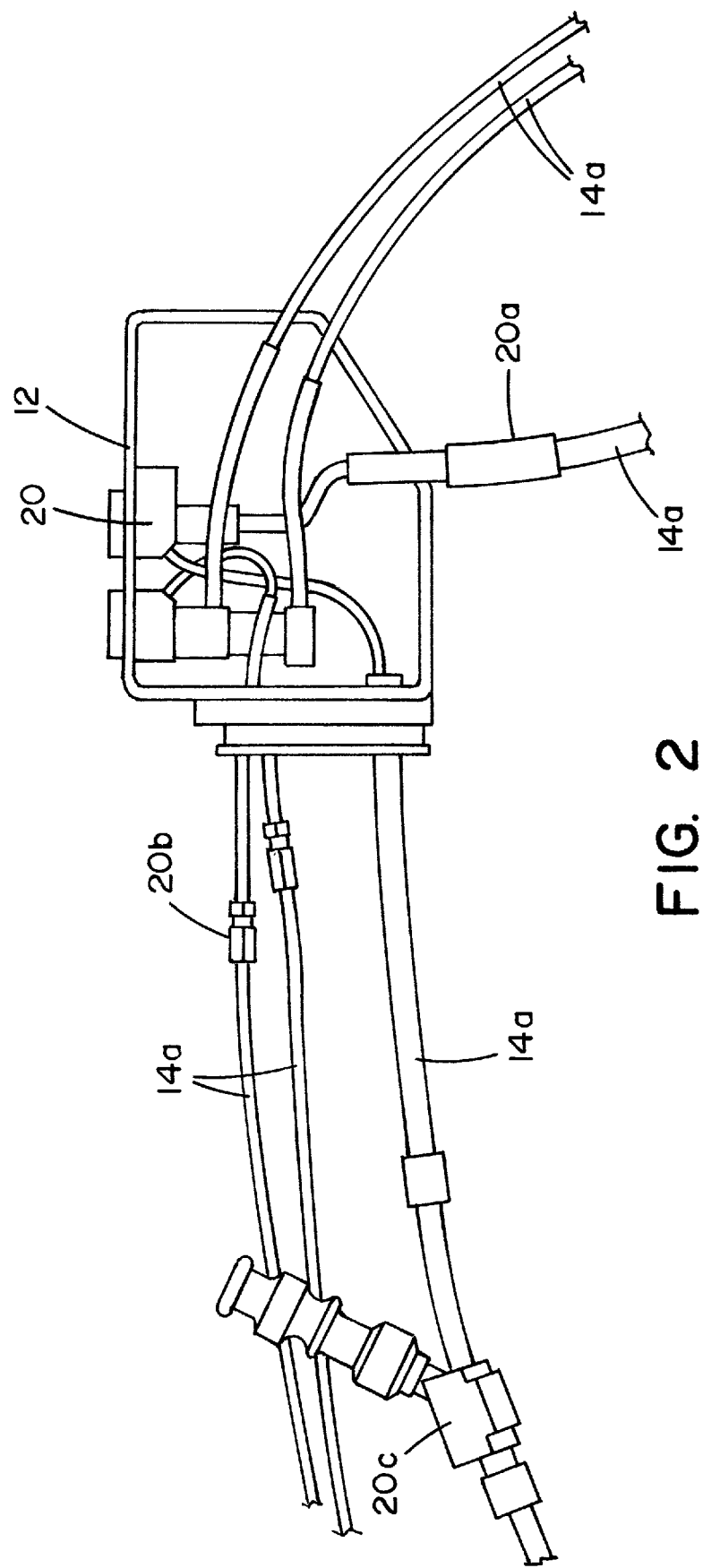
FIG. 2 is close up of an exemplary valve cylinder area showing an overview connection of tubing to valve cylinders of an exemplary test instrument in accordance with the invention.
Figure 3:
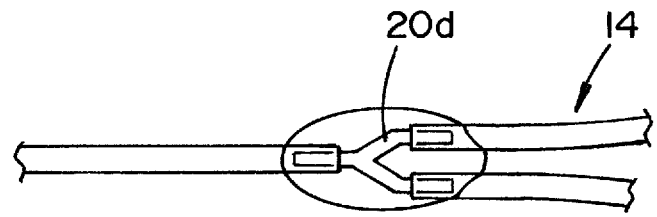
FIG. 3 illustrates an exemplary access device in accordance with the invention in the form of a Y connector.
Figure 4:
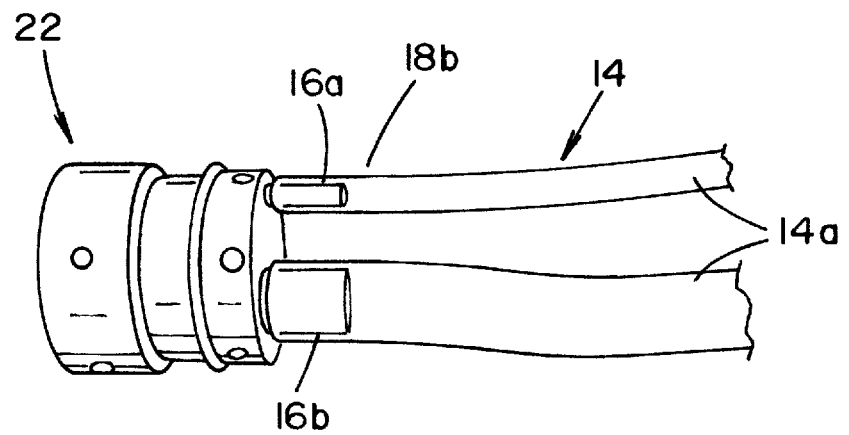
FIG. 4 illustrates an exemplary probe tip showing ports connected to internal channels in accordance with the present invention.

With additional reference to FIGS. 2-4, an access device 20 is connected to a respective flexible internal channel 14a. Non-limiting examples of access devices include a tube connector 20a (e.g., an internal connection that joins at least two flexible internal channels to each other), a screw fitting 20b (which is similar to the tube connector 20a but includes a male threaded connector at one end and a female threaded connector at the other end to hold two sections of tubing together), an instrument channel port 20c (which is a component of the flexible endoscope that connects to the exterior of the device), a "Y" connector 20d (e.g., a connector that combines a first internal channel and a second internal channel into a common third internal channel), a quick connector, or the like. It is noted that the access devices 20 may be part of the original instrument design or may be added to the instrument to replace portions for specific test purposes, e.g., for removal of sections of the instrument for destructive testing or as part of the tubing used to grow biofilm. Each access device 20 is configured to enable selective access into the respective channel 14a for placement of contaminants within the channel 14a, for joining and/or reconfiguring channel segments to each other, and/or for removing portions of a channel for analysis. For example, the access device 20 may be opened or otherwise disconnected to enable insertion of a contaminant into the flexible channel 14a and/or removal of a contaminant from the flexible internal channel 14a. Further, the access device 20 may enable portions of the flexible internal channel 14a to be easily replaced in the event they become damaged and/or are destroyed during evaluation of the decontamination process.

A probe tip 22 is connected to a distal end 18b of the flexible probe section 14, the probe tip 22 including one or more ports 16a, 16b connected to a respective flexible internal channel 14a, which may be part of a nozzle. The ports 16a, 16b provide external access to the channels 14a (e.g., external access for air, suction and/or water channels of the test instrument 10).

Figure 5:
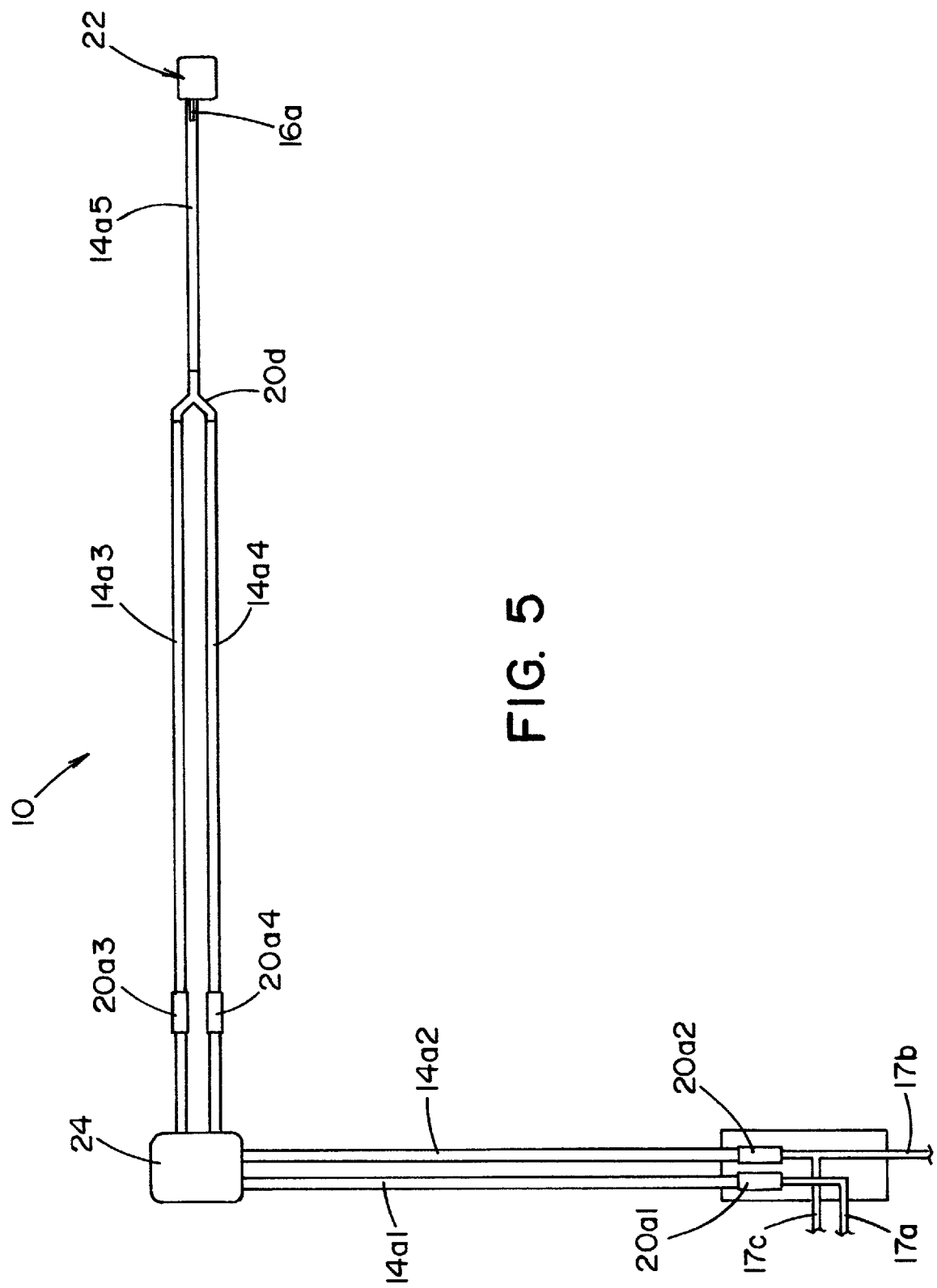
FIG. 5 is a schematic diagram illustrating exemplary air/water channels of an exemplary test instrument in accordance with the invention.

Referring now to FIG. 5, illustrated is an air/water schematic diagram of flexible channels 14a of an exemplary test instrument 10 in accordance with the present invention. As shown in FIG. 5, the exemplary test instrument 10 includes first and second tube connectors 20a1, 20a2 for connecting to air and water channels, such as a water supply connector 17a and an air supply connector 17c. The exemplary test instrument 10 also includes an air pipe 17b, which connects to an air source. A split to the air supply connector 17b pressurizes a water bottle to push water through the flexible internal channel 14a1 when a valve on the control handle 12 is actuated. A port of the water supply connector 17a is fluidically connected to a first port of an air/water valve cylinder 24 (which may be located within the handle 12—not shown in FIG. 5), via connector 20a1 and a first replaceable flexible channel 14a1, and ports of the air supply connector 17c and the air pipe 17b are fluidically connected to a second port of the air/water valve cylinder 24 via connector 20a2 and a second replaceable flexible channel 14a2. Third and fourth ports of the cylinder 24, which selectively controls the flow of water and air based on user input, are fluidically connected to first and second ports, respectively, of Y connector 20d via third and fourth replaceable flexible channels 14a3 and 14a4 and third and fourth tube connectors 20a3 and 20a4. A third port of the Y connector 20d is fluidically connected to a first exterior port 16a of the tip 22 via a fifth flexible channel 14a5, thus combining the air and water channels into a common channel that is in communication with the external port 16a of the test instrument 10. The tube connectors 20a1, 20a2, 20a3, 20a4 provide a means for configuring and/or replacing the replaceable channels 14a1, 14a2, 14a3, 14a4 of the test instrument 10.

Figure 6:
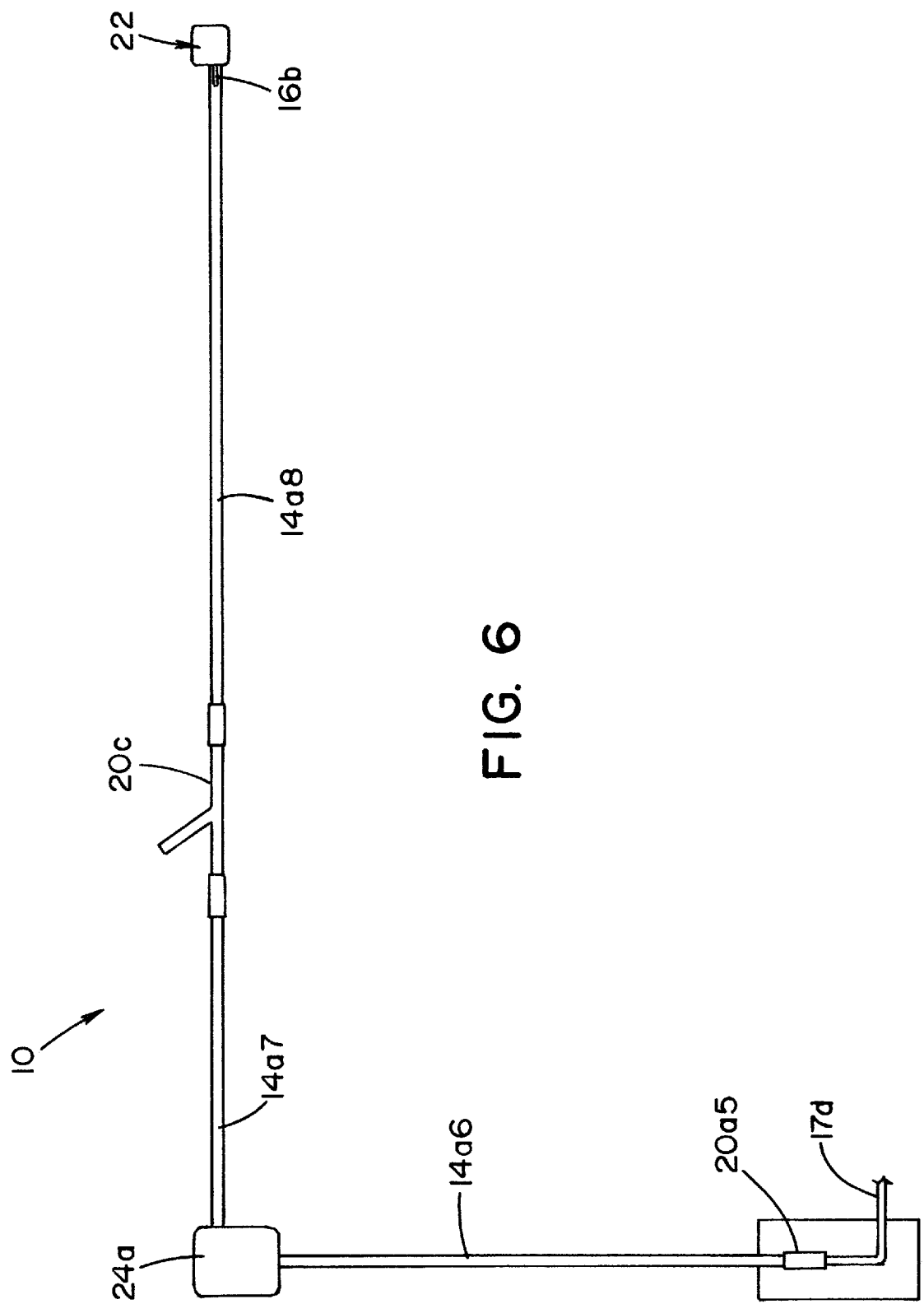
FIG. 6 is a schematic diagram illustrating exemplary suction/instrument channels of an exemplary test instrument in accordance with the invention.

Referring to FIG. 6, illustrated is a suction/instrument channel schematic diagram of the exemplary test instrument 10 in accordance with the present invention. As seen in FIG. 6, a suction connector 17d is fluidically connected to a first port of a suction valve cylinder 24a via a sixth replaceable flexible channel 14a6 and a tube connector 20a5. A second port of the suction valve cylinder 24a is fluidically connected to a first port of an instrument channel port 20c via a seventh replaceable flexible channel 14a7. A second port of the instrument channel port 20c is fluidically connected to a second port 16b of the distal tip 22 via an eighth replaceable flexible channel 14a8. The instrument channel port 20c includes a third port that can be selectively opened to gain access into the portion coupling channel 14a7 to channel 14a8 for insertion of a contaminant and/or for connection of a tube portion that includes a biofilm.

The test instrument 10 for evaluating decontamination processes of internal flexible channels 14a may be produced using a medical instrument, such as an endoscope or like instrument that includes a flexible probe section 14 having at least one internal flexible channel 14a. In one embodiment of forming the test instrument 10, an exterior covering or sheath is removed from the flexible probe section 14 to expose connections to an external device port 16 and/or the internal flexible channel 14a of the medical device. An access device 20 then is inserted between the external device port 16 and the internal flexible channel 14a to enable selective access to the internal flexible channel. A tubing connector, quick connector, a threaded connector, an instrument channel port, or any device that enables selective access into the channel 14a may be used as the access device 20. In another embodiment, at least a portion of the flexible probe section 14 of the medical instrument is discarded and a new flexible probe section is constructed using tubing, such as Teflon® tubing or other like tubing, in combination with access devices 20 to connect to ports of the medical instrument and to provide access into channels of the tubing. In this regard, the access devices 20 can be located at predetermined positions along the tubing.

The test instrument 10 may be used to evaluate the effectiveness of various decontamination processes. FIG. 7 illustrates a matrix of different contaminants, the process used to remove or destroy the contaminants, and the method used to evaluate the effectiveness of the process. For example, a contaminant may be introduced into to at least a portion of the test instrument 10. In this regard, the contaminant may be in the form of a fluid that is introduced into one or more flexible channels 14a through an access device 20. Additionally or alternatively, the contaminant may be in the form of a liquid inoculum or biological indicators containing a challenge organism that is placed into one or more channels 14a. In yet another variant, the contaminant may be in the form of a biofilm grown within a section of tubing that is attached to an access device 20 or inserted between sections of the flexible channel 14a.

The contaminants may be introduced into the channels 14a in a number of different ways. For example, one or more access devices 20 of the test instrument may be opened and the contaminant inserted through the opening and into the channels (e.g., a fluid such as colored water or alcohol, a biological indicator or a liquid inoculum may be inserted into the channel via the access device 20). When the contaminant is a biofilm grown within a section of tubing, the tubing can be connected to the channels 14a via the access device 20 (e.g., a tubing connector) or otherwise inserted into a channel 14a. When the contaminant is in the form of a liquid inoculum, a section of tubing may be connected to the access device 20 and used to direct the liquid inoculum to a challenge site in the channel 14a.

After the contaminant is introduced into the test instrument 10, a removal/destruction step then may be performed to remove the contaminant or otherwise render it harmless. If the contaminant is in the form of a liquid, the removal/destruction step may include exposing the test instrument 10 to a drying process (e.g., placing the instrument in a drying cabinet and performing a drying cycle). In this regard, forced air may be run over and through the test instrument 10 to remove the liquid. Additionally, the forced air may be heated to provide a disinfecting effect. If the contaminant is in the form of a biological indicator or liquid inoculum, the removal/destruction step may include flushing a disinfecting/sterilizing agent through the test instrument 10, including through the channels 14a. Finally, if the contaminant is in the form of a biofilm, the removal/destruction step may involve flowing a fluid (e.g., a liquid or gas) through the test instrument 10, the solution intended to remove or otherwise inactivate the biofilm.

Once the removal/destruction step is complete, the test instrument 10 may be evaluated to determine if the removal/destruction step achieved a desired result, e.g., the amount of the contaminant remaining in the test instrument 10 is less than a prescribed level. For a contaminant in the form of a fluid, the evaluation may include performing a visual inspection for residual contaminant in at least one channel 14a. For example, the evaluation may be to visually inspect the test instrument 10 to determine if any fluid remains in the channels 14a. To facilitate such evaluation, it is preferable that the tubing forming the channels 14a is clear/transparent tubing and the fluid is dyed to make viewing easier. Alternatively or additionally, the presence of the contaminant in the test instrument 10 may be based on a weight of the test instrument 10 before introducing the contaminant and a weight of the test instrument 10 after performing the decontamination step. If the weight after the removal step is higher than prior to the contamination step, it may be concluded that at least some of the contaminant is still in the test instrument 10. Yet another means for determining if contaminant in the form of a fluid is present in the test instrument is to expose the test instrument 10 to dry compressed air and capture residual contaminant expelled from the test instrument 10 (e.g., capturing any residual on a mirror, treated paper, white absorptive paper or containment device such as a jar).

If the contaminant is in the form of a biological indicator, evaluating the test instrument 10 after the decontamination step may involve removing the biological indicators from the test instrument and placing the removed biological indicators into a culture media. For example, a portion of the channel 14a is cut near the biological indicator, the biological indicator is removed using sterile forceps and placed into a tube of culture media. The effectiveness of the removal/destruction step then may be evaluated based on whether any organism growth develops in the culture media. If the contaminant is in the form of a liquid inoculum, a portion of the channel 14a that contains the liquid inoculum can be excised and placed in a culture media.

If the contaminant is in the form of a biofilm, then the evaluation may include removing the introduced section of tubing form the test article and cutting it into pieces. The pieces then can be evaluated via microscopy, for example scanning electron microscopy (SEM), for any remaining biofilm. Alternatively, sections of the test instrument 10 may be flushed with a harvest media and the harvest media can be collected. The collected harvest media then can be analyzed for presence of a predetermined components (e.g., total organic carbon, protein, hemoglobin, carbohydrate, etc.) that are indicative of the biofilm being present in the test instrument. Additionally, the harvest media may be placed in a growth media and evaluated for further growth. Yet another means for evaluating for the presence of the biofilm may be to apply a biofilm stain to the test instrument, where the biofilm stain may produce or change color in the presence of the biofilm to identify the presence of the biofilm. If the stain produces or changes color, then it can be concluded that the biofilm is present.

The test instrument in accordance with the invention enables decontamination evaluations to be easily performed on a device that mimics an actual medical instrument.

The foregoing descriptions are example embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A method for producing a test instrument used to evaluate decontamination process that includes at least one of a cleaning, disinfection or drying process of internal flexible channels, comprising:
    obtaining a medical instrument having a flexible probe section configured for insertion into a body, the flexible probe section including at least one internal flexible channel and at least one external device port; and
    attaching an access device between the at least one external device port and the at least one internal flexible channel to enable selective access into the internal flexible channel, wherein attaching the access device comprises removing an exterior sheath from the flexible probe section to expose the at least one external device port and the at least one internal flexible channel of the medical instrument.

2. The method according to claim 1, wherein attaching the access device comprises using at least one of a tubing connector or a threaded connector as the access device.

3. The method according to claim 1, wherein obtaining the medical instrument comprises obtaining a medical instrument that has at least one of exceeded a predetermined service life or become inoperable.

4. The method according to claim 1, wherein the medical instrument comprises a handle section for operating the medical instrument, the handle section connected to the flexible probe section, wherein attaching the access device comprises placing the access device within the handle section.

5. The method according to claim 4, wherein attaching the access device comprises attaching a valve cylinder in the handle section to provide selective access to the at least one channel.

6. The method according to claim 1, wherein obtaining the medical instrument comprises obtaining a flexible endoscope having a flexible probe section with a distal end surface configured for insertion into a body, the distal end surface including one external port of the at least one external port fluidically coupled to one internal channel of the at least one internal channel.

7. The method according to claim 1, wherein the at least one external port comprises at least one of a port for outputting a liquid, port for outputting air, or a port for evacuating the fluid or the air.

8. A method for producing a test instrument used to evaluate decontamination process that includes at least one of a cleaning, disinfection or drying process of internal flexible channels, comprising:
    obtaining a medical instrument having a flexible probe section configured for insertion into a body, the flexible probe section including at least one internal flexible channel and at least one external device port; and
    attaching an access device between the at least one external device port and the at least one internal flexible channel to enable selective access into the internal flexible channel, wherein attaching the access device comprises replacing the flexible probe section with transparent tubing, the transparent tubing defining the at least one flexible internal channel.

9. A method for evaluating internal flexible endoscope channels, comprising:
    producing a test instrument by obtaining a medical instrument having a flexible probe section configured for insertion into a body, the flexible probe section including at least one internal flexible channel and at least one external device port. and attaching an access device between the at least one external device port and the at least one internal flexible channel to enable selective access into the internal flexible channel. wherein attaching the access device comprises removing an exterior sheath from the flexible probe section to expose the at least one external device port and the at least one internal flexible channel of the medical instrument;

introducing, via the access device, at least one contaminant o at least a portion of the test instrument;

performing a decontamination step on the test instrument; and evaluating the test instrument to determine if the decontamination step produced a predetermined level of removal/destruction of the contaminant.

10. The method according to claim 9, wherein introducing the at least one contaminant comprises introducing a fluid into the test instrument.

11. The method according to claim 10, wherein performing the decontamination step comprises exposing the test instrument to a drying process.

12. The method according to claim 9, wherein evaluating the test instrument comprises at least one of performing a visual inspection for residual contaminant in the at least one channel, determining the presence of the at least one contaminant in the test instrument based on a weight of the test instrument before introducing the at least one contaminant and a weight of the test instrument after performing the decontamination step, or exposing the test instrument to dry compressed air and capturing residual contaminant expelled from the test instrument.

13. The method according to claim 9, wherein introducing the at least one contaminant comprises placing at least one of a liquid inoculum or biological indicators containing a challenge organism into the test instrument.

14. The method according to claim 13, wherein placing the biological indicators comprises inserting the at least one of the liquid inoculum or biological indicators into the test instrument via the access device.

15. The method according to claim 14, wherein inserting the biological indicators comprises opening the access device and inserting the at least one of the liquid inoculum or the biological indicators into the at least one channel of the test instrument via the access device.

16. The method according to claim 13, wherein performing the decontamination step comprises disinfecting the test instrument.

17. The method according to claim 13, wherein evaluating the test instrument comprises removing the biological indicators from the test instrument and placing the removed biological indicators into a culture media.

18. The method according to claim 9, wherein introducing the at least one contaminant comprises growing a biofilm within a section of tubing, and inserting the tubing into the test instrument.

19. The method according to claim 18, wherein performing the decontamination step comprises removing the biofilm from the test instrument.

20. The method according to claim 18, wherein evaluating the test instrument comprises at least one of evaluating the test instrument for remaining biofilm, flushing sections of the test instrument with a harvest media and evaluating the flushed harvest media for the presence of a predetermined components, placing the removed biofilm in a growth media and evaluating for further growth, or applying a biofilm stain to identify the presence of the biofilm.

21. The method according to claim 9, wherein the access device comprises at least one of a screw fitting or a quick connect of the test instrument.

22. A test instrument for performing at least one of a cleaning, sterilization, or drying evaluation, comprising:

a handle;

a flexible probe configured for insertion into a body, the flexible probe including a proximal end connected to the handle, at least one port, and at least one flexible internal channel, the at least one port connecting the at least one flexible internal channel to an exterior of the test instrument; and an access device connected to the at least one internal channel and configured to enable selective access into the at least one flexible internal channel for insertion and/or removal of a contaminant, wherein an exterior sheath of the flexible probe section has been removed to expose the at least one external device port and the at least one internal flexible channel of the medical instrument, and the access device is installed at the exposed region of the at least one internal flexible channel.

23. The test instrument according to claim 22, further comprising a tip connected to a distal end of the flexible probe section, the tip including the at least one port.

24. The test instrument according to claim 22, wherein the access device comprises a removable junction connecting a first internal channel to both a second internal channel and a third internal channel.

25. The test instrument according to claim 24, wherein the removable junction comprises a Y junction.

26. The test instrument according to claim 24, wherein the removable junction comprises a two-port removable connector that joins at least two flexible internal channels to each other.

27. The test instrument according to claim 22, wherein the access devices enables visual access into the at least one flexible internal channel.

* * * * *